(12) United States Patent
Davis

(10) Patent No.: US 9,053,219 B2
(45) Date of Patent: Jun. 9, 2015

(54) PATIENT MONITORING SYSTEM AND METHOD

(75) Inventor: Carl Claude Davis, Menomonee Falls, WI (US)

(73) Assignee: General Electric Company, Schenectady, NY (US)

(*) Notice: Subject to any disclaimer, the term of this patent is extended or adjusted under 35 U.S.C. 154(b) by 68 days.

(21) Appl. No.: 13/616,827

(22) Filed: Sep. 14, 2012

(65) Prior Publication Data

US 2014/0081957 A1    Mar. 20, 2014

(51) Int. Cl.
*G06F 7/00* (2006.01)
*G06F 19/00* (2011.01)

(52) U.S. Cl.
CPC .............. *G06F 19/3406* (2013.01); *G06F 19/30* (2013.01)

(58) Field of Classification Search
CPC .................... G06F 17/30581; G06F 17/30575; G06F 17/30; G06F 17/30578; G06F 17/30067; G06F 17/30749; G06F 11/1451; G06F 17/00; G06F 17/30017; G06F 19/3418; G06F 19/327; G06F 19/322; G06F 19/325; G06F 19/345; G06F 19/3468; G06F 19/324; H04L 67/1095; H04L 67/306; H04L 12/58; H04L 65/4084; H04L 67/06; H04L 67/24; H04L 12/5855
USPC ......................................................... 707/621
See application file for complete search history.

(56) References Cited

U.S. PATENT DOCUMENTS

| | | | |
|---|---|---|---|
| 2008/0082357 A1* | 4/2008 | Schmitt et al. ..................... | 705/2 |
| 2010/0131482 A1 | 5/2010 | Linthicum et al. | |
| 2011/0301982 A1* | 12/2011 | Green et al. ....................... | 705/3 |
| 2014/0025393 A1* | 1/2014 | Wang et al. ....................... | 705/2 |

FOREIGN PATENT DOCUMENTS

| | | |
|---|---|---|
| WO | 2005034001 A1 | 4/2005 |
| WO | 2011095949 A1 | 8/2011 |

OTHER PUBLICATIONS

European Search Report and Written Opinion from EP Application No. 13184292.4 dated Jan. 17, 2014.
McGrath, Susan P., "ARTEMIS: A Vision for Remote Triage and Emergency Management Information Integration", Jan. 1, 2004, pp. 1-9; URL: http://www.ists.dartmouth.edu/library/15.pdf.
Becker, K et al., "Fuzzy Logic Approaches to Intelligent Alarms", IEEE Engineering in Medicine and Biology Magazine, IEEE Service Center, Pisacataway, New Jersey, US, vol. 13, No. 5, Nov. 1, 1994, pp. 710-716.

* cited by examiner

*Primary Examiner* — Truong Vo

(57) ABSTRACT

A patient monitoring system is disclosed herein. The patient monitoring system includes a processor configured to receive CDS search data, and to identify relevant CDS options based on the search data. The patient monitoring system also includes a display operatively connected to the processor. The display is configured to convey the relevant CDS options.

11 Claims, 3 Drawing Sheets

PATIENT MONITORING SYSTEM AND METHOD

BACKGROUND OF THE INVENTION

Patient monitoring systems help a user such as a physician or technician monitor and diagnose patients. Patient monitoring systems are generally configurable to monitor one or more different patient parameters such as heart rate, blood pressure, body temperature, and saturation of peripheral oxygen (SpO2). Accordingly, a given patient monitoring system may comprise multiple monitoring subsystems such as an electrocardiograph, a blood pressure monitor, a thermometer, and/or a pulse oximeter. Many patient monitoring systems implement clinical decision support (CDS) as a means to provide user guidance.

One problem with conventional patient monitoring systems is that it is difficult to provide meaningful feedback pertaining to the potentially numerous monitored parameters and CDS guidance and visualization options on a single display. In other words, the patient monitoring systems can convey more information and guidance options than a typical user can conveniently access.

BRIEF DESCRIPTION OF THE INVENTION

The above-mentioned shortcomings, disadvantages and problems are addressed herein which will be understood by reading and understanding the following specification.

In an embodiment, a patient monitoring system includes a processor configured to receive CDS search data, and to identify relevant CDS options based on the search data. The patient monitoring system also includes a display operatively connected to the processor. The display is configured to convey the relevant CDS options.

In another embodiment, a patient monitoring system includes a monitor apparatus configured to monitor a plurality of parameters, and a touch screen display operatively connected to the monitor apparatus. The patient monitoring system also includes a processor operatively connected to the touch screen display. The processor is configured to receive CDS search data related to one of the plurality of parameters, to identify relevant CDS options based on the search data, and transmit the relevant CDS options to the touch screen. The touch screen is configured to convey the relevant CDS options from the processor.

In another embodiment, a method includes receiving CDS search data, implementing a processor to identify relevant CDS options based on the CDS search data, implementing a processor to rank the relevant CDS options, and conveying the relevant CDS options in accordance with their rank.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
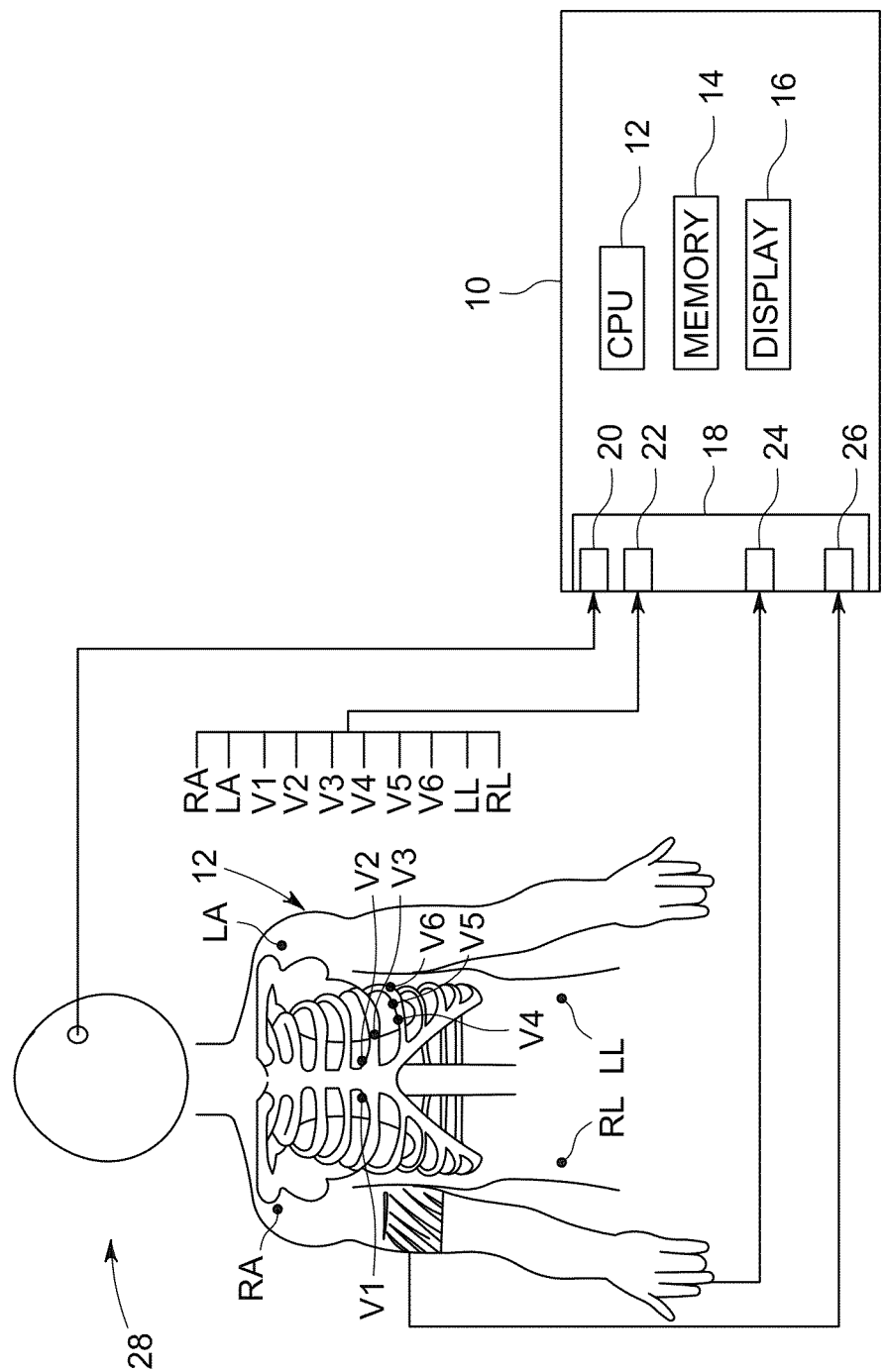
FIG. 1 is a schematic representation of a patient monitoring system in accordance with an embodiment.

Referring to FIG. 1, a monitoring system 10 is shown in accordance with one embodiment. The monitoring system 10 will hereinafter be described in accordance with an exemplary embodiment as comprising a multi-parameter patient monitoring system. The specific parameters to be monitored are configurable based on the needs of a specific patient but will hereinafter be described for illustrative purposes as including temperature, cardiac electrical activity, blood pressure and saturation of peripheral oxygen (SpO2).

The exemplary monitoring system 10 includes a central processing unit (CPU) or processor 12, a memory 14 a display 16, and a monitor apparatus 18 comprising one or more parameter monitors 20-26. The processor 12 may receive data from the parameter monitors 20-26 and process the data in a known manner. The processor 12 may transmit the processed data to the memory device 14 for storage, and/or the display 16 for communication to a user.

The processor 12 may also be configured to provide clinical decision support (CDS). In a non-limiting manner, CDS should be defined to include any feedback or guidance adapted to facilitate patient diagnosis and/or treatment. As a non-limiting example, CDS may include trending formulations or representations; visualizations; predictive algorithms; protocols; and recommendations or guidance.

The display 16 will hereinafter be described in accordance with an exemplary embodiment as comprising a touch screen display adapted to recognize contact or close proximity inputs such as touch and drag commands. For purposes of this disclosure, the concept of "touching" a touch screen display should be defined in a non-limiting manner to include any direct or indirect contact with the display. The concept of "multi-touch" should be defined in a non-limiting manner to include establishing contact with the display two or more times during the course of a single gesture. The term "contact" as applied to a touch screen display should be defined in a non-limiting manner to include both engagement with the display and close proximity to the display. The concept of "dragging" across a touch screen display should be defined in a non-limiting manner to including maintaining direct or indirect contact with the display while transitioning across the screen from an initial point of contact to a terminal point.

The display 16 can convey information from the parameter monitors 20-26 and associated user options in a known manner. It should be appreciated that it can be difficult to convey the volume of available data and associated options in a convenient manner. In other words, the display 16 may become so crowded with data that it is difficult to quickly locate specific information or user options. It is known to implement a menu structure in part to minimize the amount of information displayed at any given time. These menus, however, can also be difficult and time consuming to navigate. One particular problem with conventional systems relates to the difficulty of quickly and conveniently locating CDS options made available through a monitor display. Another problem relates to the difficulty associated with conveniently making a user aware of all the potentially relevant CDS options that are available.

The parameter monitors 20-26 will hereinafter be described in a non-limiting manner as comprising specific exemplary devices. It should, however, be appreciated that the monitoring system 10 may alternately comprise any known monitoring devices. The parameter monitor 20 may comprise a digital thermometer configured to monitor a patient's body temperature and will hereinafter be referred to as the thermometer 20. The parameter monitor 22 may comprise an electrocardiogram (ECG) acquisition device adapted to measure a patient's cardiac electrical activity and will hereinafter be referred to as the ECG acquisition device 22. The parameter monitor 24 may comprise a non-invasive blood pressure (NIBP) measurement system adapted to monitor a patient's blood pressure and will hereinafter be referred to as the NIBP system 24. The parameter monitor 26 may comprise a pulse oximetry system adapted to measure SpO2 and will hereinafter be referred to as the SpO2 system 26.

The thermometer 20 may comprise a digital temperature sensor secured to a patient 28 near the patient's temporal artery and configured to measure core body temperature. Other known devices may be implemented to measure patient temperature at any of a variety known acquisition sites.

The ECG acquisition device 22 can be coupled to the patient 28 by an array of sensors or transducers. In the illustrated embodiment, the array of sensors include a right arm electrode RA; a left arm electrode LA; chest electrodes V1, V2, V3, V4, V5 and V6; a right leg electrode RL; and a left electrode leg LL for acquiring a standard twelve lead, ten-electrode ECG signal. The twelve ECG leads include leads I, II, V1, V2, V3, V4, V5 and V6 which can be acquired directly from the patient leads, and leads III, aVR, aVL and aVF which can be derived using Einthoven's law. In other embodiments, alternative configurations of sensors and sensor locations can be used to acquire a standard or non-standard ECG signal.

The NIBP system 24 may comprise an inflatable cuff secured to the patient's arm, and a transducer adapted to measure pressure oscillations within the cuff. These measured oscillations are correlated with and may be used to calculate the patient's blood pressure. Other known blood pressure measurement devices including but not limited to invasive blood pressure monitoring systems may alternatively be implemented.

The SpO2 system 26 may comprise an emitter configured to pass light of multiple different wavelengths through the patient's finger. The SpO2 system measures the changing absorbance of the multiple wavelengths to determine the saturation of peripheral oxygen. Other known devices may be implemented to measure oxygenated hemoglobin at any of a variety known acquisition sites.

Figure 2:
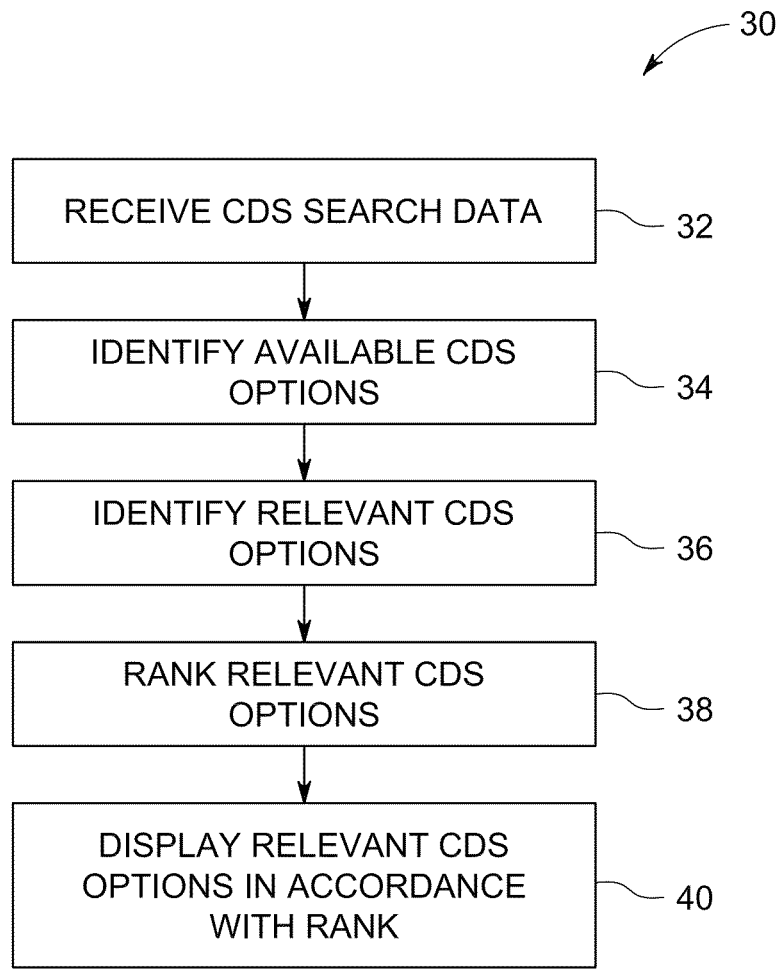
FIG. 2 is a flow chart illustrating a method in accordance with an embodiment.

FIG. 2 is a flow diagram representing an exemplary algorithm 30 that may be carried out by the patient monitoring system 10. The algorithm 30 may comprise instructions, such as software or code, contained in one or more non-transient computer-readable mediums or persistent storage devices such as the memory 14. The algorithm 30 will hereinafter be described in accordance with an embodiment as comprising steps 32-40 which may be performed by the processor 12 and/or display 16. Some of the steps 32-40 may be optional, and they need not necessarily be performed in the order shown.

The algorithm 30 will be described in accordance with an embodiment as being configured to help a user quickly and conveniently locate CDS options available through the display 16. At step 32, the algorithm 30 receives CDS search data. The search data may comprise any data provided to help find a relevant CDS option. According to one embodiment, the search data comprises one or more user identified monitored parameters selected as being components of or related to the searched CDS option. The search data may also comprise the sequence or manner in which the monitored parameters are selected. For example, the monitored parameters carbon dioxide (CO2); heart rate; and respiration rate may be identified by a user in order to find CDS related to patient weaning. The sequence or manner in which these parameters are identified may indicate a priority such that the first parameter identified (CO2) is given additional weight in the search for relevant CDS options.

At step 34, the algorithm 30 identifies available CDS options. The available CDS options may, for example, be identified by accessing a database or list of all possible CDS options available for a specific monitoring system. The list of available CDS options may be narrowed by eliminating those requiring input from inactive parameters. As an example, the algorithm 30 could eliminate all CDS options requiring SpO2 as an input if the patient monitoring system 10 (shown in FIG. 1) is not actively monitoring SpO2.

At step 36, the algorithm 30 identifies relevant CDS options based on the search data from step 32 and the available CDS options from step 34. According to an embodiment in which the search data comprises user identified monitored parameters, step 36 may be executed by identifying any CDS options comprising or related to the identified monitored parameters. Referring again to a previous example, the algorithm 30 may identify a weaning CDS option in response to user input search data comprising CO2, heart rate and respiration rate.

At step 38, the algorithm 30 may rank potentially relevant CDS options. The CDS options may be ranked in any known manner including but not limited to a priority based on the degree of alignment with the search data and/or historic CDS option usage rates. At step 40, the relevant CDS options identified at step 36 are displayed. These options are preferably displayed via the monitoring system display 16 in accordance with their ranking as established at step 38.

Figure 3:
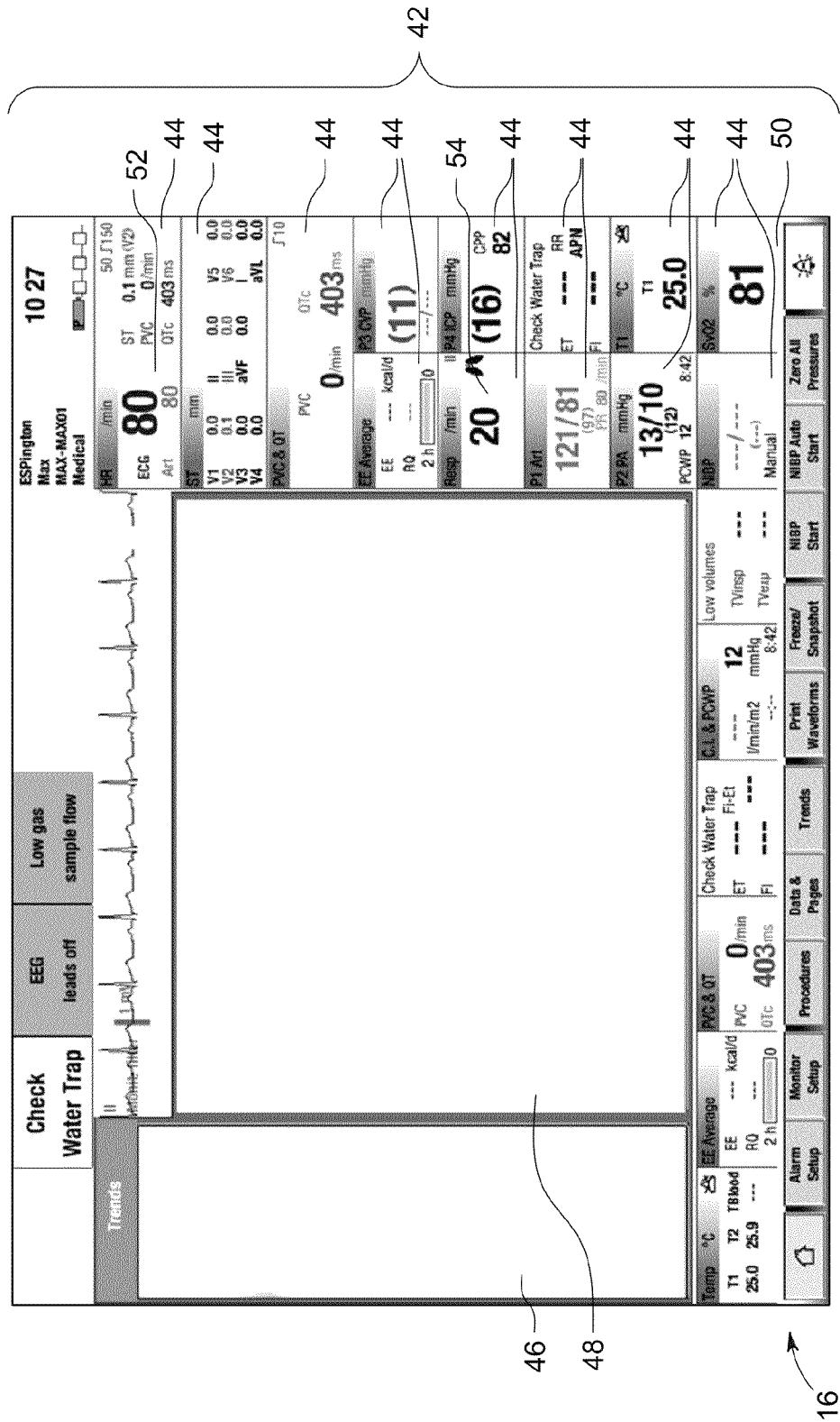
FIG. 3 is a representation of a patient monitoring system display in accordance with an embodiment.

Referring to FIG. 3, the monitoring system display 16 is shown in accordance with an embodiment to illustrate an exemplary method for implementing the algorithm 30 (shown in FIG. 2) to help locate CDS options.

The display 16 may comprise multiple regions dedicated to specific purposes. For example, the region 42 comprise a plurality of parameter blocks 44 adapted to convey monitored parameter data from one or more of the parameter monitors 20-26. The region 46 may accept user inputs. The region 48 may convey CDS options or a selected CDS display. The parameter blocks 44 may comprise a CO2 parameter block 50, a heart rate parameter block 52, and a respiration rate parameter block 54.

A user wanting help locating a specific CDS option may implement the display 16 in the following manner. The user may touch individual parameter blocks from region 42 and drag them into region 46. The specific parameters touched and dragged in this manner, and the sequence in which they are selected may serve as search data inputs required for step 32 of the algorithm 30 (shown in FIG. 2). For example, a user searching for weaning CDS options may touch CO2 parameter block 50 and drag it into region 46; then touch heart rate parameter block 52 and drag it in into region 46; and then touch respiration rate parameter block 54 and drag it into region 46. The algorithm 30 may assign a higher priority to the CO2 parameter block input as it was identified first. Based on this search data, the algorithm 30 (shown in FIG. 2) may then identify all CDS options (e.g., weaning) comprising the CO2, heart rate and respiration rate parameters.

As another example, a user may touch one individual parameter block from region 42, drag it onto another parameter block also within region 42, and then touch and drag the superimposed parameters into region 46 as part of a multi-touch gesture. The algorithm 30 may assign a higher priority to the individual parameter block identified first.

After ranking the CDS options at step 38, the algorithm 30 (shown in FIG. 2) may display the ranked list of CDS options in region 48. A user can select an appropriate CDS option from the ranked list by touching it. The selected CDS option can then be conveyed in region 48 in place of the ranked list. It should be appreciated that this intuitive approach to locating available CDS options can save considerable time that would otherwise be required for an unassisted search.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A patient monitoring system comprising:
   a processor configured to
      receive Clinical Decision Support (CDS) search data comprising one or more user-selected monitored parameters and a sequence in which the one or more user-selected monitored parameters are selected;
      identify relevant CDS options based on the search data, wherein the CDS options are at least one of trending formulations or representations, visualizations, predictive algorithms, protocols and recommendations or guidance; and
      rank the identified relevant CDS options by priority based on correspondence to the CDS search data; and
   a display operatively connected to the processor, the display configured to convey
   a list of the ranked CDS options.

2. The patient monitoring system of claim 1, wherein the display comprises a touch screen display.

3. The patient monitoring system of claim 2, wherein the user-selected monitored parameters may be selected by touching a first region of the touch screen display and dragging to a second region.

4. The patient monitoring system of claim 3, wherein the user-selected monitored parameters may be selected by touching multiple points of contact within the first region as part of a multi-touch gesture.

5. The patient monitoring system of claim 3, wherein the first region of the touch screen display is generally dedicated to conveying an output related to a plurality of monitored parameters, and wherein the second region is generally dedicated to receiving the CDS search data.

6. The patient monitoring system of claim 4, wherein a first user-identified monitored parameter is selected by touching a first parameter block at a first point of contact within the first region and a second user-identified monitored parameter is selected by dragging the first parameter block into a second parameter block.

7. A patient monitoring system comprising:
   a monitor apparatus configured to monitor a plurality of parameters;
   a touch screen display operatively connected to the monitor apparatus; and
   a processor operatively connected to the touch screen display, the processor configured to
      receive Clinical Decision Support (CDS) search data comprising one or more user-selected parameters of the plurality of parameters and a sequence in which the one or more user-selected parameters are selected;
      identify relevant CDS options based on the search data, wherein the CDS options are at least one of trending formulations or representations, visualizations, predictive algorithms, protocols and recommendations or guidance;
      rank the identified relevant CDS options by priority based on correspondence to the CDS search data; and
      transmit the relevant CDS options to the touch screen display;
   wherein the touch screen display is configured to convey a list of the ranked CDS options from the processor.

8. The patient monitoring system of claim 7, wherein the CDS search data may be selected by touching a point within a first region of the touch screen display and dragging to a second region.

9. The patient monitoring system of claim 8, wherein the touched point corresponds to one of the plurality of parameters.

10. A method comprising:
    receiving Clinical Decision Support (CDS) search data comprising one or more user-selected monitored parameters and a sequence in which the one or more user-selected monitored parameters are selected;
    implementing a processor to identify relevant CDS options based on the CDS search data;
    implementing a processor to rank the relevant CDS options by priority based on correspondence to the CDS search data; and
    conveying the relevant CDS options in accordance with their rank.

11. The patient monitoring system of claim 10, wherein the CDS options are at least one of trending formulations or representations, visualizations, predictive algorithms, protocols and recommendations or guidance.

* * * * *